United States Patent [19]

Aoyama et al.

[11] Patent Number: 5,424,204
[45] Date of Patent: Jun. 13, 1995

[54] METHOD FOR STABILIZING GLUCOSE 6-PHOSPHATE DEHYDROGENASE WITH HYDROXYLAMINES, ALDEHYDE SCAVENGERS, DIMETHYLTHIOCARBAMOYL CHLORIDE OR 2-(2-AMINOETHYLAMINO) ETHANOL

[75] Inventors: Norihito Aoyama; Minako Sakakibara, both of Shizuoka, Japan

[73] Assignee: Kyowa Medex Co., Ltd., Tokyo, Japan

[21] Appl. No.: 294,586

[22] Filed: Aug. 23, 1994

[30] Foreign Application Priority Data

Aug. 26, 1993 [JP] Japan ................... 5-211202

[51] Int. Cl.6 .................. C12N 9/96; C12N 9/04; C12Q 1/54; C12Q 1/32
[52] U.S. Cl. .................. 435/188; 435/190; 435/14; 435/26
[58] Field of Search .................. 435/190, 188, 14, 26

[56] References Cited

U.S. PATENT DOCUMENTS

| | | | |
|---|---|---|---|
| 4,036,697 | 7/1977 | Pierre et al. | 435/15 |
| 4,080,262 | 3/1978 | Beaucamp et al. | 435/188 |
| 4,118,279 | 10/1978 | Defermann et al. | 435/188 |
| 4,189,536 | 2/1980 | Green | 435/12 |
| 4,229,369 | 10/1980 | Green | 260/501.19 |
| 4,271,264 | 6/1981 | Modrovich | 435/14 |
| 4,438,199 | 11/1984 | Miwa et al. | 435/190 |
| 4,816,391 | 3/1989 | Khanna | 435/7 |
| 4,897,346 | 1/1990 | Gawronski | 435/14 |
| 4,990,445 | 2/1991 | Poudrier et al. | 435/22 |
| 5,200,399 | 4/1993 | Wettlaufer et al. | 514/23 |
| 5,231,004 | 7/1993 | Warren, III et al. | 435/7.36 |
| 5,290,765 | 3/1994 | Wettlaufer et al. | 514/23 |

FOREIGN PATENT DOCUMENTS

| | | |
|---|---|---|
| 0119722 | 2/1984 | European Pat. Off. . |
| 0253520 | 1/1988 | European Pat. Off. . |
| 253520 | 1/1988 | European Pat. Off. . |
| 456309 | 11/1991 | European Pat. Off. . |
| WO93/00807 | 1/1993 | WIPO . |

OTHER PUBLICATIONS

Sawiniec et al., Diagn. Lab. (1974), 10(8), 203–10.
Glader et al., J. Lab. Clin. Med., 1973, 81(2), 267–72.
Bashan et al., Israel J. Med. Sci., 16(5), 351–56.
Tilton et al., Clin. Pharm. Ther., 15(2), 1974, 221.
Park, Yonsei J. of Med. Sci., 4(2), 1971, 118–237.
Gibson et al., Analytica Chimica Acta, 279 (1993) 185–192.

Primary Examiner—David M. Naff
Assistant Examiner—Mike Meller
Attorney, Agent, or Firm—Nixon & Vanderhye

[57] ABSTRACT

Glucose 6-phosphate dehydrogenase is stabilized in a clinical assay reagent with at least one stabilizer selected from among hydroxylamines, aldehyde scavengers dimethylthiocarbamoyl chloride, 2-(2-aminoethylamine) ethanol, and their salts. The reagent may be in liquid or lyophilized form.

4 Claims, No Drawings

METHOD FOR STABILIZING GLUCOSE 6-PHOSPHATE DEHYDROGENASE WITH HYDROXYLAMINES, ALDEHYDE SCAVENGERS, DIMETHYLTHIOCARBAMOYL CHLORIDE OR 2-(2-AMINOETHYLAMINO) ETHANOL

FIELD OF THE INVENTION

This invention relates to a method for stabilizing glucose 6-phosphate dehydrogenase and a clinical assay reagent composition containing stabilized glucose 6-phosphate dehydrogenase.

BACKGROUND OF THE INVENTION

Glucose 6-phosphate dehydrogenase is an enzyme catalyzing a reaction of, in the presence of a coenzyme nicotinamide adenine dinucleotide (hereinafter referred to simply as NAD) or nicotinamide adenine dinucleotide phosphate (hereinafter referred to simply as NADP), oxidizing glucose 6-phosphate into glucono-δ-lactone 6-phosphate and reduced nicotinamide adenine dinucleotide (hereinafter referred to simply as NADH) or reduced nicotinamide adenine dinucleotide phosphate (hereinafter referred to simply as NADPH) or vice versa. This enzyme is widely distributed in the natural world. Although glucose 6-phosphate dehydrogenase has been used in determining glucose-related substances and coenzymes or measuring the activities of glucose-related enzymes in clinical specimens using this function, it lacks stability for practical applications.

Various procedures have been described to improve the stability of glucose 6-phosphate dehydrogenase such as using an enzyme originating in a thermophilic bacterium (see JP-A-56-169598 corresponding to U.S. Pat. No. 4,438,199 and JP-A-59-151899 corresponding to EP-A-119 722, the term "JP-A" as used herein means an "unexamined published Japanese patent application"). Satisfactory stability is not reliably achieved by these methods.

It has also suggested to stabilize glucose 6-phosphate dehydrogenase with a chelating agent or an SH compound in a reagent for assaying glucose (see EP-A-253 520), however satisfactory stability is not achieved in a weakly acidic region.

SUMMARY OF THE INVENTION

It is an object of the present invention to stabilize glucose 6-phosphate dehydrogenase in a liquid clinical assay reagent, which is used for quantitatively determining the amount of a glucose-related substance or coenzyme or measuring the activity of a glucose-related enzyme.

The present invention provides a method for stabilizing glucose 6-phosphate dehydrogenase by adding to glucose 6-phosphate dehydrogenase at least one stabilizer selected from among hydroxylamines, aldehyde scavengers and their salts.

DETAILED DESCRIPTION OF THE INVENTION

The hydroxylamine used in the present invention is a compound represented by formula (I) [hereinafter referred to simply as the compound (I)]:

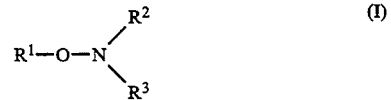

where $R^1$, $R^2$ and $R^3$ may be either the same or different and each represents a hydrogen atom, a substituted or unsubstituted lower alkyl group, a cycloalkyl group, a lower alkenyl group, a substituted or unsubstituted aralkyl group, a substituted or unsubstituted aryl group, a lower alkanoyl group, a substituted or unsubstituted aroyl group, a cinnamyl group or a cinnamoyl group, or $R^2$ and $R^3$ together form a nitrogen-containing heterocyclic group by interposing a nitrogen atom.

The aldehyde scavenger used in the present invention is a compound selected from a compound represented by formula (II) [hereinafter referred to simply as the compound (II)]:

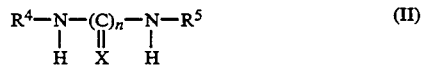

where $R^4$ and $R^5$ may be either the same or different and each represents a hydrogen atom, a substituted or unsubstituted lower alkyl group, a cycloalkyl group, a lower alkenyl group, a substituted or unsubstituted aralkyl group, a substituted or unsubstituted aryl group, a substituted or unsubstituted heterocyclic group, a lower alkanoyl group, a substituted or unsubstituted aroyl group, a pyridylcarbonyl group, a lower alkoxycarbonyl group or a substituted or unsubstituted amino group; X represents an oxygen atom or a sulfur atom and n is an integer of 0 to 2, $(CH_3)NCSCl$ [hereinafter referred to as the compound (III)] and $H_2NCH_2CH_2NCH_2CH_2OH$ [hereinafter referred to as the compound (IV)].

In the definition of the compounds (I) and (II), the alkyl moiety in the lower alkyl and lower alkoxycarbonyl groups means straight or branched ones having 1 to 6 carbon atoms, for example, methyl, ethyl, propyl, isopropyl, butyl, isobutyl, sec-butyl, tert-butyl, pentyl, neopentyl and hexyl groups. The cycloalkyl group means those having 3 to 8 carbon atoms such as cyclopropyl, cyclobutyl, cyclopentyl, cyclohexyl, cycloheptyl and cyclooctyl groups. The lower alkenyl group means straight or branched ones having 2 to 6 carbon atoms such as vinyl, allyl, isopropenyl, 4-pentenyl and 5-hexenyl groups. The aralkyl group means those having 7 to 15 carbon atoms such as benzyl, phenethyl, benzhydryl and phenylpropyl groups. The aryl group and the aryl moiety in the aroyl group mean phenyl and naphthyl groups. The nitrogen-containing heterocyclic group formed by $R^2$ together with $R^3$ includes, for example, pyrrolidinyl, piperidino, morpholino and piperazinyl groups; the heterocyclic group includes, for example, furyl, thienyl, pyrrolyl, pyranyl, thiopyranyl, pyridyl, thiazolyl, imidazolidinyl, pyrimidinyl, triazinyl, indolyl, quinolyl, purinyl and benzothiazolyl groups; and the lower alkanoyl group includes linear or branched ones having 1 to 6 carbon atoms such as formyl, acetyl, propionyl, butyryl, valeryl, pivaloyl and pentanoyl groups.

The substituents for the lower alkyl group may be either the same or different from each other. For example, 1 to 3 substituents selected from among hydroxyl, lower alkoxyl, carboxyl, lower alkoxycarbonyl, lower alkylthio, halogen, amino, mono- or di-substituted amino and phthalimido groups and nitrogen-containing heterocyclic groups such as pyrrolidinyl, pyrazolyl and indolyl groups may be cited where the alkyl moiety in the lower alkoxyl, lower alkoxycarbonyl, lower alkylthio and alkyl-substituted amino groups has the same meaning as the one defined above while halogen is fluorine, chlorine, bromine and iodine.

The substituents for the aralkyl, aryl and aroyl groups and the heterocyclic group may be either the same or different from each other. For example, 1 to 5 substituents selected from lower alkyl, hydroxyl, lower alkoxyl, halogen, nitro and amino groups may be cited where the alkyl moiety in the lower alkyl and lower alkoxyl groups has the same meaning as defined above and halogen also has the same meaning as defined above.

The substituents for the substituted amino group may be either the same or different from each other. For example, 1 or 2 substituents selected from among lower alkyl, aralkyl, substituted or unsubstituted aryl, lower alkanoyl, substituted or unsubstituted aroyl and alkylidene groups, each having the same meaning as the one defined above, may be cited. The alkylidene group means linear or branched ones having 1 to 6 carbon atoms such as methylene, ethylidene, propylidene, isopropylidene, butylidene, isobutylidene, secbutylidene, tert-butylidene, pentylidene, neopentylidene and hexylidene groups.

Examples of the salts of the hydroxylamines and the aldehyde scavengers include inorganic acid salts such as hydrochloride, hydrobromide, sulfate, nitrate, nitrite and phosphate, organic acid salts such as oxalate, acetate, succinate, fumarate, maleate, tartarate and citrate and base addition salts such as sodium and potassium salts.

Particular examples of the compounds (I) and (II) are given below in Tables 1 and 3 identified by names while Tables 2 and 4 shows the structural formulae. The names of the compounds (III) and (IV) are respectively dimethylthiocarbamoyl chloride and 2-(2-aminoethylamino) ethanol.

TABLE 1

| Compound No. | Name |
|---|---|
| I-1 | hydroxylamine hydrochloride |
| I-2 | hydroxylamine sulfate |
| I-3 | hydroxylamine oxalate |
| I-4 | carboxymethoxylamine hydrochloride |
| I-5 | O-benzylhydroxylamine hydrochloride |
| I-6 | N-benzoyl-N-phenylhydroxylamine |
| I-7 | N-benzoyl-N-(2-methylphenyl)hydroxylamine |
| I-8 | N-cinnamoyl-N-phenylhydroxylamine |
| I-9 | N-methylhydroxylamine |
| I-10 | O-methylhydroxylamine |
| I-11 | N-cinnamoyl-N-2,3-xylylhydroxylamine |
| I-12 | N-(tert-butyl)hydroxylamine |
| I-13 | N-cyclohexylhydroxylamine hydrochloride |

TABLE 2

$$R^1-O-N\begin{matrix}R^2\\R^3\end{matrix}$$

| Compound No. | R$^1$ | R$^2$ | R$^3$ |
|---|---|---|---|
| I-1* | H | H | H |
| I-2** | H | H | H |
| I-3*** | H | H | H |
| I-4* | HOOCCH$_2$ | H | H |
| I-5* | C$_6$H$_5$CH$_2$ | H | H |
| I-6 | H | C$_6$H$_5$ | C$_6$H$_5$CO |
| I-7 | H | 2-methylphenyl (CH$_3$) | C$_6$H$_5$CO |
| I-8 | H | C$_6$H$_5$ | C$_6$H$_5$CH=CHCO |
| I-9 | H | CH$_3$ | H |
| I-10 | CH$_3$ | H | H |
| I-11 | H | 2,3-xylyl (H$_3$C, CH$_3$) | C$_6$H$_5$CH=CHCO |
| I-12 | H | (CH$_3$)$_3$C | H |
| I-13* | H | 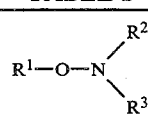 cyclohexyl | H |

*hydrochloride.
**sulfate.
***oxalate.

TABLE 3

| Compound No. | Name |
|---|---|
| II-1 | benzoylhydrazine |
| II-2 | pentafluorophenylhydrazine |
| II-3 | oxalyldihydrazide |
| II-4 | nicotinic acid hydrazide |
| II-5 | ethylhydrazinoaceate hydrochloride |
| II-6 | 2-hydrazino-2-imidazoline hydrobromide |
| II-7 | 3-hydroxy-2-naphthoenic acid hydrazide |
| II-8 | methyl carbazate |
| II-9 | 1-acetylthiosemicarbazide |
| II-10 | diphenylcarbazide |
| II-11 | diphenylthiocarbazide |
| II-12 | ethyl carbazate |
| II-13 | 4-ethyl-3-thiosemicarbazide |
| II-14 | 4-phenylsemicarbazide |
| II-15 | iproniazide |
| II-16 | acetone thiosemicarbazone |
| II-17 | dithiooxyamide |

TABLE 4

$$R^4-N-(C)_n-N-R^5$$
$$\;\;\;\;|\;\;\;\;||\;\;\;\;|$$
$$\;\;\;\;H\;\;\;X\;\;\;H$$

| Compound No. | n | X | R$^4$ | R$^5$ |
|---|---|---|---|---|
| II-1 | 0 | — | C$_6$H$_5$CO | H |
| II-2 | 0 | — | C$_6$F$_5$ | H |
| II-3 | 2 | O | H$_2$N | NH$_2$ |
| II-4 | 0 | — | 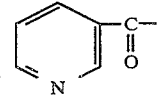 pyridine-C(=O) | H |

TABLE 4-continued

R⁴—N—(C)ₙ—N—R⁵
    |    ||    |
    H   X   H

| Compound No. | n | X | R⁴ | R⁵ |
|---|---|---|---|---|
| II-5 | 0 | — | C₂H₅OCOCH₂ | H |
| II-6 | 0 | — | 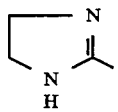 | H |
| II-7 | 0 | — | 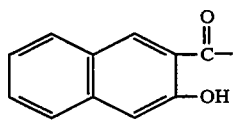 | H |
| II-8 | 0 | — | CH₃OCO | H |
| II-9 | 1 | S | CH₃CONH | H |
| II-10 | 1 | O | C₆H₅NH | NHC₆H₅ |
| II-11 | 1 | S | C₆H₅NH | NHC₆H₅ |
| II-12 | 0 | — | C₂H₅OCO | H |
| II-13 | 1 | S | C₂H₅ | NH₂ |
| II-14 | 1 | O | C₆H₅ | NH₂ |
| II-15 | 0 | — | 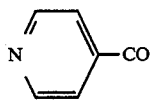 | CHCH₃<br>\|<br>CH₃ |
| II-16 | 1 | S | (CH₃)₂C=N | H |
| II-17 | 2 | S | H | H |

These hydroxylamines, aldehyde scavengers and their salts listed in Tables 1 to 4 and compounds (III) and (IV) are all known compounds and available from commercial suppliers, for example, Aldrich and Dojin Kagaku Kenkyusho.

The activity of any glucose 6-phosphate dehydrogenase can be stabilized according to the present invention. Specifically, the glucose 6-phosphate dehydrogenase to be stabilized according to the present invention may be arbitrarily selected from among those originating in microorganisms such as *Leuconostoc mesenteroides, Bacillus stearothermophilus, Azotobacter vinelandii* and *Pseudomonas fluorescens*, yeasts, animals and plants.

In order to stabilize glucose 6-phosphate dehydrogenase, at least one stabilizer selected from among hydroxylamines and their salts and aldehyde scavengers and their salts may be formulated with glucose 6-phosphate dehydrogenase in an amount of from $1 \times 10^{-8}$ to $1 \times 10^{-2}$ mol/U of glucose 6-phosphate dehydrogenase (international unit), preferably from $4 \times 10^{-7}$ to $1 \times 10^{-4}$ mol/U.

The stabilizer exhibits a satisfactory effect even when used either alone or in combination.

The present invention also relates to an assay reagent composition for quantitatively determining the amount of a glucose-related substance or coenzyme or measuring the activity of a glucose-related enzyme. The assay reagent composition comprises glucose 6-phosphate dehydrogenase, a stabilizing amount of at least one stabilizer selected from among hydroxylamines, aldehyde scavengers and their salts. The amounts of the glucose 6-phosphate dehydrogenase and the stabilizer to be contained in the composition are the same as described for the above stabilizing method.

As the glucose-related substance and coenzyme, which can be determined using the assay reagent, and the glucose-related enzyme, the activity of which can also be determined with the use of this reagent, any substance which can be converted into glucose 6-phosphate, i.e., a substrate of glucose 6-phosphate dehydrogenase may be used.

Examples of the glucose-related substances include lactose, maltose, glycogen, starch, sucrose, glucose, fructose, mannose, creatine phosphate, glucose 6-phosphate, fructose 6-phosphate, maltose 6-phosphate, fructose 2-phosphate, L-sorbose 6-phosphate, glucose 1-phosphate and uridine diphosphate glucose.

Examples of the glucose-related coenzymes include NAD, NADP, uridine triphosphate and adenosine triphosphate.

Examples of the glucose-related enzymes include creatine kinase, hexokinase, glucokinase, β-galactosidase, α-galactosidase, amyloglucosidase, invertase, transaldolase, galactose 1-phosphate uridyltransferase, phosphoglucose isomerase and fructose diphosphatase.

The assay reagent composition may be in the form of either a liquid or a partly or totally lyophilized state. The lyophilized assay reagent composition is dissolved in a solvent such as a buffer solution just prior to use. The glucose 6-phosphate dehydrogenase and the stabilizer may be lyophilized or in the form of a solution or in both either.

The buffer includes, for example, tris hydrochloride buffer, imidazole acetate buffer, phosphate buffer, citrate buffer, malate buffer, oxalate buffer, phthalate buffer, glycine buffer, acetate buffer, succinate buffer, borate buffer, carbonate buffer or Good's buffer. The buffer is adjusted to a concentration of from 0.005 to 2 mol/l and pH of from 3 to 11, preferably from 5 to 9.

The assay reagent composition contains glucose 6-phosphate dehydrogenase in a concentration of from 0.1 to 100 U/ml, preferably from 1 to 25 U/ml, and at least one stabilizer selected from among hydroxylamines and their salts and aldehyde scavengers and their salts in a concentration of from 0.001 to 1 mol/l, preferably from 0.01 to 0.1 mol/l.

The assay reagent composition may further contain other enzymes, coenzymes chromogenic agents, surfactants, chelating agents, other stabilizers and other substances.

Examples of other enzymes include the glucose-related enzymes as cited above, nucleosidediphosphate kinase, peroxidase, NAD(P)H oxidase, ascorbate oxidase, catalase, bilirubin oxidase and uricase. Examples of coenzymes include the glucose-related coenzymes as cited above, tetrahydrofolic acid and pyridoxal phosphate. Examples of chromogenic agents include those used for the direct color development of NAD(P)H, for example, tetrazolium salts such as tetrazolium blue and nitrotetrazolium blue and those for conversion into hydrogen peroxide followed by the color development, for example, single reagents such as o-dianisidine, 4-methoxy-1-naphthol and 2,2'-azino-bis(3-ethylbenzothiazoline)-6-sulfonic acid, reagents containing 4-aminoantipyrine combined with phenol compounds such as phenol, p-chlorophenol and 2,4,6-tribromophenol, aniline compounds such as N,N-dimethylaniline and N,N-diethylaniline or toluidine compounds such as N,N-diethyl-m-toluidine, a reagent containing 3-methyl-2-benzothiazolinohydrazine combined with N,N-dimethylaniline, and compounds described in JP-A-57-29297 corresponding to U.S. Pat. No. 4,384,042 or JP-A-59-74713 corresponding to EP-A-124 287 may be used in the presence of peroxidase. Surfactants such as polyethylene glycol mono-p-iso-octylphenyl ether, chelating agents such as ethylenediaminetetraacetic acid, other stabilizers such as albumin may be used. Examples of the other substances include the glucose-related substances as cited above, salts such as magnesium acetate or amino acid.

Examples of the assay reagent composition include composition 1 for quantitatively determining the amount of glucose and composition 2 for measuring the activity creatine kinase, which are described as follows.

| Composition 1: | |
|---|---|
| imidazole acetate buffer (pH 6.6) | 20–500 mM |
| tris hydrochloride buffer (pH 8.7) | 20–500 mM |
| magnesium chloride | 0.1–50 mM |
| hexokinase | 0.1–20 U/ml |
| glucose 6-phosphate dehydrogenase | 0.1–20 U/ml |
| NADP | 0.2–20 mM |
| adenosine-5'-triphosphate disidium salt | 0.1–20 mM |
| stabilizer selected from hydroxylamines, aldehyde scavengers and their salts | 0.1–50 mM |
| Composition 2 | |
| imidazoleacetate buffer (pH 6.6) | 20–500 mM |
| ethylenediaminetetraacetic acid | 0–50 mM |
| magnesium acetate | 0.1–50 mM |
| N-acetylcysteine | 5–100 mM |
| adenosine diphosphate | 1–20 mM |
| adenosine monophosphate | 1–20 mM |
| adenosine pentaphosphate | 1–50 µM |
| glucose | 5–100 mM |
| NADP | 0.2–20 mM |
| hexokinase | 0.1–20 U/ml |
| glucose 6-phosphate dehydrogenase | 0.1–20 U/ml |
| creatine phosphate | 10–150 U/ml |
| stabilizer selected from hydroxylamines, aldehyde scavengers and their salts | 0.1–50 mM |

To further illustrate the present invention in greater detail, the following Examples will be given but are not to be construed to limit the scope of the present invention.

EXAMPLE 1

Stabilization of glucose 6-phosphate dehydrogenase in a reagent for measuring the activity of creatine kinase Reagent solutions 1 and 2 were prepared as an assay reagent composition for measuring the activity of creatine kinase.

| Reagent solution 1: | |
|---|---|
| imidazole-acetate buffer (pH 6.6) | 115 mM |
| ethylenediaminetetraacetic acid | 2.3 mM |
| magnesium acetate | 11.5 mM |
| N-acetylcysteine | 23 mM |
| adenosine diphosphate | 2.3 mM |
| adenosine monophosphate | 5.8 mM |
| adenosine pentaphosphate | 11.5 µM |
| glucose | 23 mM |
| NADP | 2.3 mM |
| hexokinase | 3.45 U/ml |
| glucose 6-phosphate dehydrogenase | 1.725 U/ml |
| Reagent solution 2: | |
| creatine phosphate | 345 mM |

To examine the effect of stabilizing glucose 6-phosphate dehydrogenase, 10 mM portions of compounds (I-1 to 13), compounds (II-1 to 17), compound (III) and compound (IV) were each added to the reagent solution 1 and then stored at 10° C. As a control, reagent solution 1 containing no additive was also stored at 10° C. Glucose 6-phosphate dehydrogenase activity of the reagent solution 1 containing each additive was measured immediately after the preparation of the reagent and after storing for 3 and 12 months.

Glucose 6-phosphate dehydrogenase activity was measured by adding glucose 6-phosphate dehydrogenase to a reaction solution containing D-glucose 6-phosphate as a substrate and NADP as a coenzyme and measuring the amount of NADPH thus formed in terms of a change in absorbance at 340 nm. From the glucose 6-phosphate dehydrogenase activity data thus obtained, the residual activities after storing for 3 and 12 months were calculated by referring to the activity immediately after the preparation of the reagent as 100%. Table 5 shows the results.

TABLE 5

| Compound No. | Residual activity after 3 months (%) | Residual Activity after 12 months (%) |
|---|---|---|
| I-1 | 100.2 | 85.9 |
| I-2 | 99.8 | 88.7 |
| I-3 | 98.2 | 89.2 |
| I-4 | 99.9 | 88.9 |
| I-5 | 96.8 | 78.9 |
| I-6 | 80.5 | 30.3 |
| I-7 | 81.5 | 25.6 |
| I-8 | 90.4 | 44.5 |
| I-9 | 100.1 | 80.3 |
| I-10 | 99.7 | 82.3 |
| I-11 | 79.6 | 23.6 |
| I-12 | 75.5 | 22.2 |
| I-13 | 92.1 | 80.2 |
| II-1 | 100.1 | 87.6 |
| II-2 | 85.6 | 40.3 |
| II-3 | 88.5 | 65.2 |
| II-4 | 70.3 | 38.5 |
| II-5 | 75.4 | 28.3 |
| II-6 | 89.2 | 58.5 |
| II-7 | 89.7 | 60.3 |
| II-8 | 99.8 | 86.5 |
| II-9 | 82.3 | 45.6 |
| II-10 | 85.5 | 39.2 |
| II-11 | 87.3 | 40.5 |
| II-12 | 102.2 | 88.3 |
| II-13 | 90.2 | 62.1 |
| II-14 | 99.9 | 86.5 |
| II-15 | 65.8 | 20.1 |
| II-16 | 79.8 | 41.5 |
| II-17 | 75.2 | 32.3 |
| III | 80.3 | 43.2 |
| IV | 98.7 | 81.1 |
| control (none) | 61.1 | 7.4 |

EXAMPLE 2

Assay Reagent Composition The following composition consisting of Reagent solutions 1 and 2 was prepared for quantitatively determining the amount of glucose.

| Reagent solution 1 | |
|---|---|
| imidazole-acetate buffer (pH 6.6) | 115 mM |
| magnesium chloride | 18 mM |
| hexokinase | 3.3 U/ml |
| glucose 6-phosphate dehydrogenase | 0.93 U/ml |
| NADP | 2.77 mM |
| hydroxylamine hydrochloride | 10 mM |
| Reagent solution 2 | |
| tris hydrochloride buffer (pH 8.7) | 100 mM |
| adenosine-5'-triphosphate disidium salt | 3.47 mM. |

According to the present invention, the stability of glucose 6-phosphate dehydrogenase in a liquid clinical assay reagent, which is used for determining a glucose-related substance and coenzyme or measuring the activity of a glucose-related enzyme can be remarkably improved.

While the invention has been described in detail and with reference to specific examples, it will be apparent to one skilled in the art that various changes and modifications can be made therein without departing from the spirit and scope of the invention.

What is claimed is:

1. A method for preparing an assay reagent containing stabilized glucose 6-phosphate dehydrogenase comprising adding to glucose 6-phosphate dehydrogenase a stabilizing amount of at least one stabilizer selected from the group consisting of dimethylthiocarbamoyl chloride, 2-(2-aminoethylamino) ethanol, a hydroxylamine which is a compound represented by formula (I):

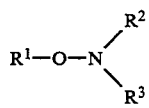
(I)

wherein $R^1$, $R^2$ and $R^3$ may be either the same or different and each represents a hydrogen atom, a substituted or unsubstituted lower alkyl group, a cycloalkyl group, a lower alkenyl group, a substituted or unsubstituted aralkyl group, a substituted or unsubstituted aryl group, a lower alkanoyl group, a substituted or unsubstituted aroyl group, a cinnamyl group or a cinnamoyl group, or $R^2$ and $R^3$ together form a nitrogen-containing heterocyclic group by interposing a nitrogen atom, an aldehyde scavenger which is a compound represented by formula (II)

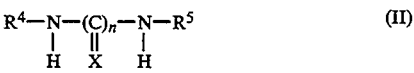
(II)

wherein $R^4$ and $R^5$ may be either the same or different and each represents a hydrogen atom, a substituted or unsubstituted lower alkyl group, a cycloalkyl group, a lower alkenyl group, a substituted or unsubstituted aralkyl group, a substituted or unsubstituted aryl group, a substituted or unsubstituted heterocyclic group, a lower alkanoyl group, a substituted or unsubstituted aroyl group, a pyridylcarbonyl group, a lower alkoxycarbonyl group or a substituted or unsubstituted amino group, X represents an oxygen atom or a sulfur atom, and n is an integer of 0 to 2, and a salt thereof to produce said assay reagent.

2. The method according to claim 1, wherein the stabilizer is in an amount from $1 \times 10^{-8}$ to $1 \times 10^{-2}$ mol/U of glucose 6-phosphate dehydrogenase.

3. A assay reagent prepared by the method of claim 1.

4. The assay reagent composition according to claim 3, wherein the stabilizer is in an amount from $1 \times 10^{-8}$ to $1 \times 10^{-2}$ mol/U of glucose 6-phosphate dehydrogenase.

* * * * *